US006987180B2

(12) United States Patent
Verdine et al.

(10) Patent No.: US 6,987,180 B2
(45) Date of Patent: Jan. 17, 2006

(54) URIDINE ANALOGS AND TECHNIQUES FOR MAKING AND USING

(75) Inventors: Gregory L. Verdine, Lexington, MA (US); Michael Storek, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 177 days.

(21) Appl. No.: 10/072,641

(22) Filed: Feb. 7, 2002

(65) Prior Publication Data

US 2003/0186930 A1 Oct. 2, 2003

(51) Int. Cl.
*C07H 19/06* (2006.01)
*C07H 19/067* (2006.01)
*C07H 19/09* (2006.01)

(52) U.S. Cl. .................. 536/28.53; 536/26.1; 536/26.2; 536/26.21; 536/26.8; 536/28.4; 536/28.54; 536/124

(58) Field of Classification Search ................. 514/42, 514/43, 44, 49, 50, 51; 536/28.4, 28.53, 536/28.54, 28.55
See application file for complete search history.

(56) References Cited

U.S. PATENT DOCUMENTS

| 4,672,111 A | | 6/1987 | Haley et al. |
|---|---|---|---|
| 4,983,727 A | * | 1/1991 | Bergstrom et al. |
| 5,215,882 A | * | 6/1993 | Bahl et al. |
| 5,241,060 A | * | 8/1993 | Engelhardt et al. |

FOREIGN PATENT DOCUMENTS

| DE | 137 110 | 8/1979 |
|---|---|---|
| WO | WO 98/00433 A1 | 1/1998 |
| WO | WO 99/08110 A1 | 2/1999 |
| WO | WO 00/18967 A1 | 4/2000 |
| WO | WO 01/07087 A2 | 2/2001 |
| WO | WO 01/07088 A2 | 2/2001 |

OTHER PUBLICATIONS

Ferrer et al., "Preparation of Oligonucleotides Containing 5-Bromouracil and 5-Methoylcytidine", *Nucleosides & Nucleotides*, vol. 15, No. 4, 1996, pp. 907-921.
Desgranges et al., "Phosphorolysis of )E)-5-(2-Bromovinyl)-2'-Deoxyuridine (BVDU) and Other 5-Substituted-2'-Deoxyuridines by Purified Human Thymidine Phosphorylase and Intact Blood Platelets", *Biochemical Pharmacology*, vol. 32, No. 23, 1983, pp. 3583-3590.
Roy-Burman, et al., "Studies on the Effect of Triphosphates of 5-Aminouridine and 5-Hydroxydeoxyuridine of Ribonucleic Acid and Deoxyribonucleic Acid Polymerases", *Biochemical Pharmacolog*, vol. 19, 1970, pp. 2745-2756.
Leung et al., " Characteristics of Deoxythymidine Transport and Deoxythymidine Kinase in 3T3 Cells", *Biochemical Medicine*, vol. 16, 1976, pp. 127-137.
Cinatl et al., "2',3'-Dideoxycytidine Preferentially Inhibits in vitro Growth of Granulocyte-Macrophage Colony-Forming Cells from Patients with Chronic Myeloid Leukemia", *Chemotherapy*, vol. 37, 1991, pp. 128-133.
Balzarini et al., "5-Substituted 2'-Deoxyuridines: Correlation Between Inhibition of Tumor Cell Growth and Inhibition of Thymidine Kinase and Thymidylate Synthetase", *Biochemical Pharmacoloy*, vol. 31, No. 22, 1982, pp. 3673-3682.
Barawkar et al., "Solid Phase Synthesis of DNA Containing 5-NH$_2$-2'-Deoxyuridine", *Bioorg. Med. Chem. Lett.*, vol. 3, 1993, pp. 347-352.
Cheng et al., "Mouse Ascites Sarcoma 180 Deoxythymidine Kinase. General Properties and Inhibition Studies", *Biochemistry*, vol. 13, No. 6, 1974, pp. 1179-1185.
Eriksson et al., "Comparison of the Substrate Specificities of Human Thymidine Kinase 1 and 2 and Deoxycytidine Kinase Toward Antiviral and Cytostatic Nucleoside Analogs", *Biochemical and Biophysical Research Communications*, vol. 176, No. 2, 1991, pp. 586-592.
Ferrer et al., "Preparation and Properties of Oligodeoxynucleotides Containing 5-Iodouracil and 5-Bromo-and 5-Iodocytosine", *Bioconjugate Chem.*, vol. 8, No. 5, 1997, pp. 757-761.
Hampton et al., Design of Species- or Isozyme-Specific Enzyme Inhibitors. 2. Differences between a Bacterial and a Mammalian Thymidine Kinase in the Effect of Thymidine Substituents on Affinity for the Thymidine Site, *J. Med. Chem.*, vol. 22, No. 12, 1979, pp. 1524-1528.
Hampton et al., "Design of Species- or Isozyme-Specific Enzyme Inhibitors. 1. Effect of Thymdine Substituents on Affinity for the Thymidine Site of Hamster Cytoplasmic Thymidine Kinase", *J. Med. Chem. Soc.*, vol. 22, No. 6, 1979, pp. 621-631.

(Continued)

Primary Examiner—James O. Wilson
Assistant Examiner—Traviss C. McIntosh, III
(74) Attorney, Agent, or Firm—Wolf, Greenfield + Sacks, P.C.

(57) ABSTRACT

Uridine analogs and techniques for making and using uridine analogs are disclosed in this invention. These uridine analogs include nucleoside phosphates having a 5-aminouracil group. These nucleotides can be incorporated into a nucleic acid as an unnatural base, as a substitute for uridine or thymine. The nucleic acid can then be treated with an oxidizing agent and an alkaline solution, which causes cleavage of the nucleic acid at the position of the unnatural base. The nucleoside phosphate analogs can be used in many ways, including measuring chemical interactions between nucleic acids and other compounds, or sequencing nucleic acids. Additional compounds can also be derivitized onto the amino group, allowing other functionalities to be added to the nucleoside phosphate, or to the nucleic acid incorporating the nucleoside phosphate.

6 Claims, 4 Drawing Sheets

OTHER PUBLICATIONS

Hampton et al., "Species- or Isozyme-Specific Enzyme Inhibitors. 5. Differential Effects of Thymidine Substituents on Affinity for Rat Thymidine Kinase Isozymes", *J. Med. Chem.*, vol. 25, No. 6, 1982, pp. 644-649.

Hayashibara et al., "Template-Directed Interference Footprinting of Cytosine Contacts in a Protein-DNA Complex: Potent Interference by 5-Aza-2'-deoxycytidine", *Biochemistry*, vol. 31, No. 46, 1992, pp. 11265-11273.

Hayashibara et al., "Template-Directed Interference Footprinting of Protein-Guanine Contacts in DNA", *J. Am. Chem. Soc.*, vol. 113, No. 13, 1991, pp. 5104-5106.

Lee et al., "Human Deoxythymidine Kinase II: Substrate Specificity and Kinetic Behavior of the Cytoplasmic and Mitochondrial Isozymes Derived from Blast Cells of Acute Myelocytic Leukemia", *Biochemistry*, vol. 15, No. 17, 1976, pp. 3686-3690.

Mascarenas et al., "Template-Directed Interference Footprinting of Protein-Thymine Contacts", *J. Med. Chem. Soc.*, vol. 115, No. 1, 1993, pp. 373-374.

Wigerinck et al., "Synthesis and Antiviral Activity of 5-Heteroaryl-Substituted 2'-Deoxyuridines", *J. Med. Chem.*, vol. 34, No. 6, 1991, pp. 1767-1772.

Barawkar et al., "Effect of C5-Amino Substituent on 2'-Deoxyuridine base pairing with 2'-Deoxyadenosine: Investigation by H and C NMR Spectroscopy", *Tetrahedron*, vol. 48, No. 39, 1992, pp. 8505-8514.

Evans et al. "Synthesis and Biological Properties of 5-Azido-2'-deoxyuridine 5'-Triphosphate, a Photoactive Nucleotide Suitable for Making Light-Sensitive DNA", *Biochemistry*, vol. 26, No. 1, 1987, pp. 269-276.

Evans et al., "5-Azido-2'-deoxyuridine 5'-triphosphate: A photoaffinity-labeling reagent and tool for the enzymatic synthesis of photoactive DNA", *Proc. Natl. Acad. Sci. USA*, vol. 83, 1986, pp. 5382-5386.

Kumar et al., "Nonradioactive Labeling of Synthetic Oligonucleotide Probes with Terminal Deoxynucleotidyl Transferase", *Analytical Biochemistry*, vol. 169, 1988, pp. 376-382.

Jadhav et al., "5-Amido-(Carboxyfluorescein)-2'-dU-Oligonucleotides: Novel Primers for Fluorescent Detection of PCR Amplified DNA", *Nucleosides & Nucleotides*, vol. 16, No. 1&2, 1997, pp. 107-114.

Dyatkina et al, "Terminating substrates of DNA polymerases: synthesis and functional study", *Symposium Series*, No. 8, 1987, pp. 117-120.

Beck et al., "Enhancement of Methotrexate Cytotoxicity by Uracil Analogues that Inhibit Deoxyuridine Triphosphate Nucleotidohydrolase (duTPhase) Activity", *Adv. Ext. Med. Biol.*, vol. 195B, 1996, pp. 97-104.

Balzarini et al., "Strucutre-Function Relationship of the Antitumor Cell Activity of Pyrimidine and Pyradine Derivatives", *Proc. Int. Roundtable Nucleosides, Nucleosides Bio. Appl.*, vol. 4, 1982, pp. 275-291.

Barawkar et al., "Effect of C5-amino substituent on 2'-deoxyuridine base pairing with 2'-deoxyadenosine: Investigation by H and C NMR spectroscopy", *Tetrahedron*, vol. 48, No. 39, 1992, pp. 8505-8514.

* cited by examiner

URIDINE ANALOGS AND TECHNIQUES FOR MAKING AND USING

BACKGROUND

1. Field of the Invention

This invention relates to uridine analogs and, in particular, to making and using nucleoside phosphates having a 5-aminouracil group.

2. Description of the Related Art

Uracil is a nucleic acid base, that, when bound to ribose or deoxyribose, forms uridine or deoxyuridine, respectively. Certain analogs of uridine and deoxyuridine have been prepared and used in different applications.

For example, deoxyribouridine analogs containing a 5-amino group have been prepared and used as anticancer, antiviral, or antibacterial agents. Such uses may be found, for example, in Shepard, Patent No. WO 2001/007088; Shepard, Patent No. WO 2001/007087; Shepard, et al., Patent No. WO 99/37753; Shepard, Patent No. WO 99/08110; Wigerinck, et al., *J. Med. Chem.*, 34:1767–1772 (1991); Cinatl, et al., *Chemotherapy*, 37:128–133 (1991); Beck, et al., *Adv. Ext. Med. Biol.*, 195B:97–104 (1996); Desgranges, et al., *Biochem. Pharmacol.*, 32:3583–3590 (1983); Balzarini, et al., *Biochem. Pharmacol.*, 31:3673–3682 (1982); Hampton, et al., *J. Med. Chem.*, 25:644–649 (1982); Balzarini, et al., *Proc. Int. Roundtable Nucleosides, Nucleotides Biol. Appl.* 4:275–291 (1982); Hampton, et al., *J. Med. Chem.*, 22:1524–1528 (1979); Hampton, et al., *J. Med. Chem.*, 22:621–631 (1979); Lee, et al., *Biochemistry*, 15:3686–3690 (1976); Leung, et al., *Biochem. Med.*, 16:127–137 (1976); Cheng, et al., *Biochemistry*, 13:1179–1185 (1974); or Roy-Burman, et al., *Biochem. Pharmacol.* 19:2745–2756 (1970). Other nucleotide analogs have been described in, for example, Verdine, et al., Patent No. WO 98/00433; Hayashibara, et al., *J. Am. Chem. Soc.*, 113:5104–5106 (1991); Hayashibara, et al., *Biochemistry*, 31:11265–11273 (1992); or Mascareñas, et al., *J. Am. Chem. Soc.*, 115:373–374 (1993).

Other 5-amino deoxyribouridine analogs have been synthesized and analyzed, for example, in Ferrer, et al., *Bioconjugate Chem.*, 8:757–761 (1997); Ferrer, et al., *Nucleosides Nucleotides*, 15:907–921 (1996); Barawkar, et al., *Bioorg. Med. Chem. Lett.*, 3:347–352 (1993); Eriksson, et al., *Biochem. Biophys. Res. Commun.*, 176:586–592 (1991); Baerwolff, German Patent No. DD 137110; or *Tetrahedron*, 48:8505–8514 (1992). In some cases, 5-amino deoxyribouridine analogs have been derivitized with fluorescent compounds, for example, in Jadhav, et al., *Nucleosides Nucleotides*, 16:107–114 (1997). 5-amino deoxyribouridine analogs have also been prepared for DNA sequence determination, such as in Dyatkina, et al., *Nucleic Acids Symp. Ser.*, 18:117–120 (1987).

SUMMARY OF THE INVENTION

The present invention relates to nucleoside phosphates having a 5-aminouracil group.

In one aspect, the invention provides a composition. In one set of embodiments, the composition comprises a structure:

where n is at least 2.

In another set of embodiments, the invention provides a composition comprising a structure:

where $R^1$ is capable of being integrated into a nucleic acid; $R^2$ is a carbon atom or a nitrogen atom; $R^3$ comprises an atom; $R^4$ and $R^5$ are capable of participating in hydrogen-bonding to adenine or an adenine analog; and at least one of $R^6$ and $R^7$ comprises an electron-rich substituent.

In another set of embodiments, the invention provides a composition comprising a structure:

where $R^1$ is capable of being integrated into a nucleic acid; each of $R^2$, $R^3$, $R^4$, $R^5$, $R^6$ and $R_7$ is a carbon atom or a nitrogen atom; at least one of $R^4$ and $R^5$ is capable of hydrogen bonding to or carries a substituent capable of hydrogen bonding to adenine or an adenine analog; and at least one of $R^6$ or $R^7$ carries an electron-rich substituent.

In each of the above embodiments, selection of $R^1$ through $R^7$ is preferably made as described below in connection with the description of FIG. 1.

It is to be understood that any and all compositions disclosed herein can be used in connection with any and all methods, and vice versa.

In another aspect, the invention provides a method of synthesizing a compound. In one set of embodiments, the method comprises the steps of providing a species comprising a nucleoside, and reacting the species with a compound to form a composition comprising a structure:

where n is at least 2.

In another set of embodiments, the invention provides a method of synthesizing a deoxyribonucleic acid. The method comprises the steps of providing a plurality of nucleotides, providing a composition comprising a structure:

where n is at least 2, and reacting the nucleotides and the composition to produce a deoxyribonucleic acid.

In another set of embodiments, the invention provides a method of synthesizing a deoxyribonucleic acid. The method comprises the steps of providing a nucleic acid comprising a base at a position within the nucleic acid, and synthesizing a deoxyribonucleic acid using the nucleic acid as a template. The base in the nucleic acid is one of thymine or uracil. The base at a position within the deoxyribonucleic acid corresponding to the position of the base within the nucleic acid is substituted by an unnatural base comprising a structure:

where R is a covalent bond.

In another set of embodiments, the invention provides a method of analyzing a deoxyribonucleic acid. The method comprises the steps of providing a deoxyribonucleic acid comprising an unnatural base, and determining a position of the unnatural base within the deoxyribonucleic acid. The unnatural base comprises a structure:

where R is a covalent bond.

In another set of embodiments, the invention provides a method of characterizing a compound. The method comprises the steps of providing a compound, contacting the compound with a deoxyribonucleic acid comprising an unnatural base, and determining a degree of binding between the compound and the deoxyribonucleic acid. The unnatural base comprises a structure:

where R is a covalent bond.

In another set of embodiments, the invention provides a method of oxidizing a deoxyribonucleic acid. The method comprises the steps of providing a deoxyribonucleic acid comprising an unnatural base, and reacting the deoxyribonucleic acid with an oxidizing agent. The unnatural base comprises a structure:

where R is a covalent bond.

In another set of embodiments, the invention provides a method of oxidizing a deoxyribonucleic acid. The method comprises the step of providing a deoxyribonucleic acid comprising an unnatural base comprising a structure:

where R is a covalent bond. The method also comprises the step of reacting the deoxyribonucleic acid with a compound to cleave double bond X.

In another set of embodiments, the invention provides a method of oxidizing a deoxyribonucleic acid. The method comprises the steps of providing a deoxyribonucleic acid comprising an unnatural base at a position within the deoxyribonucleic acid, and reacting the deoxyribonucleic acid with a compound to cleave the deoxyribonucleic acid at the position of the unnatural base. The unnatural base comprises a structure:

where R is a covalent bond.

In another set of embodiments, the invention provides a method of synthesizing an amine. The method comprises the step of providing a composition comprising a structure:

where n is at least 2. The method also comprises the step of reacting the $NH_2$ group of the composition with a compound to form an amine comprising a structure:

where at least one of $R^1$ and $R^2$ comprises a carbon atom.

In another set of embodiments, the invention provides a method of synthesizing a compound. The method comprises the step of providing a composition comprising a structure:

where n is at least 2, and coupling a reporting group to the compound.

Other advantages, novel features, and objects of the invention will become apparent from the following detailed description of the invention when considered in conjunction with the accompanying drawings, which are schematic and which are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

Non-limiting embodiments of the present invention will be described by way of example with reference to the accompanying drawings in which.

DETAILED DESCRIPTION

Uridine analogs and techniques for making and using uridine analogs are provided by the present invention. They may be used in many ways, including measuring chemical interactions between nucleic acids and other compounds, or sequencing nucleic acids. These uridine analogs may include nucleoside phosphates having a 5-aminouracil group. These nucleotides may be incorporated into a nucleic acid as an unnatural base, as a substitute for uridine or thymine. The nucleic acid may then be treated with an oxidizing agent and an alkaline solution, which may cause cleavage of the nucleic acid at the position of the unnatural base. Additional compounds may also be derivitized onto the amino group, allowing other functionalities to be added to the nucleoside phosphate, or to the nucleic acid incorporating the nucleoside phosphate.

As used herein, the term "base" is given its ordinary meaning as is understood in biochemistry and similar fields of study, referring to nucleic acids and similar compounds. Chemical bases such as sodium hydroxide will be referred to as "alkaline compounds," "alkaline materials," and the like.

"Nucleotides" and "nucleosides" are given their ordinary meanings as is understood in the field of biochemistry. A nucleoside generally includes a base and a sugar, while a nucleotide generally includes a base, a sugar, and at least one phosphate. The atoms within the base and the sugar are conventionally numbered, with primes typically indicating the atoms of the sugar group. A "natural base" may be any one of the commonly observed bases found on nucleic acids such as deoxyribonucleic acid ("DNA") or ribonucleic acid ("RNA"). These may include adenine, thymine, guanine, cytosine, or uracil. Correspondingly, an "unnatural base" is a base that is not commonly observed bases found on nucleic acids such as DNA or RNA.

A "deoxyribo-" generally indicates a ribose sugar where one of the hydroxide groups located on the ribose ring has been substituted by hydrogen. Generally, this is the 2' hydroxide group.

As used herein, "hydrocarbon," "alkyl," and similar terms includes not only alkyl groups, but also alkenyl, alkynyl, cycloalkyl, aryl, alkaryl, aralkyl, and the like. Examples of such hydrocarbon groups may include methyl, propenyl, ethynyl, cyclohexyl, phenyl, tolyl, benzyl, hydroxyethyl and the like. Hetero groups may include —O—, —CONH—, —CONHCO—, —NH—, —CSNH—, —CO—, —CS—, —S—, —SO—, —(OCH$_2$CH$_2$)$_n$— (where n may range from 1 to 10), —(CF$_2$)$_n$— (where n may range from 1 to 10), olefins, and the like. "Hydrocarbon," "alkyl," and similar terms are also meant to include alcohols and hydrogen. By way of example, the "alkyl" may comprise an alkyl group, preferably having 1 to 24 carbon atoms, more preferably 1 to 18 carbon atoms; an alkenyl group, preferably having 2 to 4 carbon atoms; an alkylamino group, preferably having 1 to 8 carbon atoms, and optionally substituted on the nitrogen atom with one or, preferably two alkyl groups, preferably having 1 to 4 carbon atoms; an alkyl group, preferably having 1 to 4 carbon atoms, having a five- or six-membered heterocyclic ring as a substitutent; an allyloxyalkyl group, preferably having up to 12 carbon atoms; an alkoxyalkyl group, preferably having a total of 2 to 12 carbon atoms; an aryloxyalkyl group, preferably having 7 to 12 carbon atoms; an aralkyl group, or the like.

As used herein, "R" may indicate not only single atoms, but groups of atoms which may be connected by any suitable bond, for example, ionic, hydrogen, van der Waals, or hydrophobic bonds. Preferably, R indicates an atom, or a group of atoms connected via covalent bonds.

The term "determining" refers to quantitative or qualitative analysis of a species via, for example, spectroscopy, radioactive counting, HPLC analysis, nuclear magnetic resonance, and the like. "Determining" also refers to detecting or quantifying interactions between species, e.g. detection of the binding between two species.

"Derivative," "analog," "chemical derivative," "derivatizing," and similar terms are given their ordinary meanings as well-known in the fields of chemistry, biochemistry, or biology. A derivative may be any chemical substance structurally related to another chemical substance and at least theoretically derivable from it. An analog may be a chemical or biological species that is similar enough to a parent species that it may substitute for the parent species in at least one set of chemical or biochemical interactions. For example, if the parent compound is a nucleic acid base, the analog may be able to substitute for the nucleic acid base, and be able to participate in reactions involving the nucleic acid base, such as hydrogen-bonding with another nucleic acid, or interactions with proteins or enzymes, such as a ribosome.

A "dalton" (Da) is an alternate name for the unified atomic mass unit (grams/mole) that is well known in biochemistry and allied fields. The dalton is accepted by SI as an alternate name for the unified atomic mass unit. Similarly, a "kilodalton" (kDa) is 1000 daltons.

"Small molecule," as used herein, typically means a molecule less than 5 kilodalton, more typically less than 1 kilodalton.

"Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids, but may be less in some cases.

A molecule "capable of integrating" into a second molecule generally refers to a molecule that can be integrated or otherwise attached to a second molecule, without requiring the use of further synthetic chemical reactions that modify the structure of the molecule into a different, stable structure, prior to introduction of the molecule into the second molecule.

Figure 1:
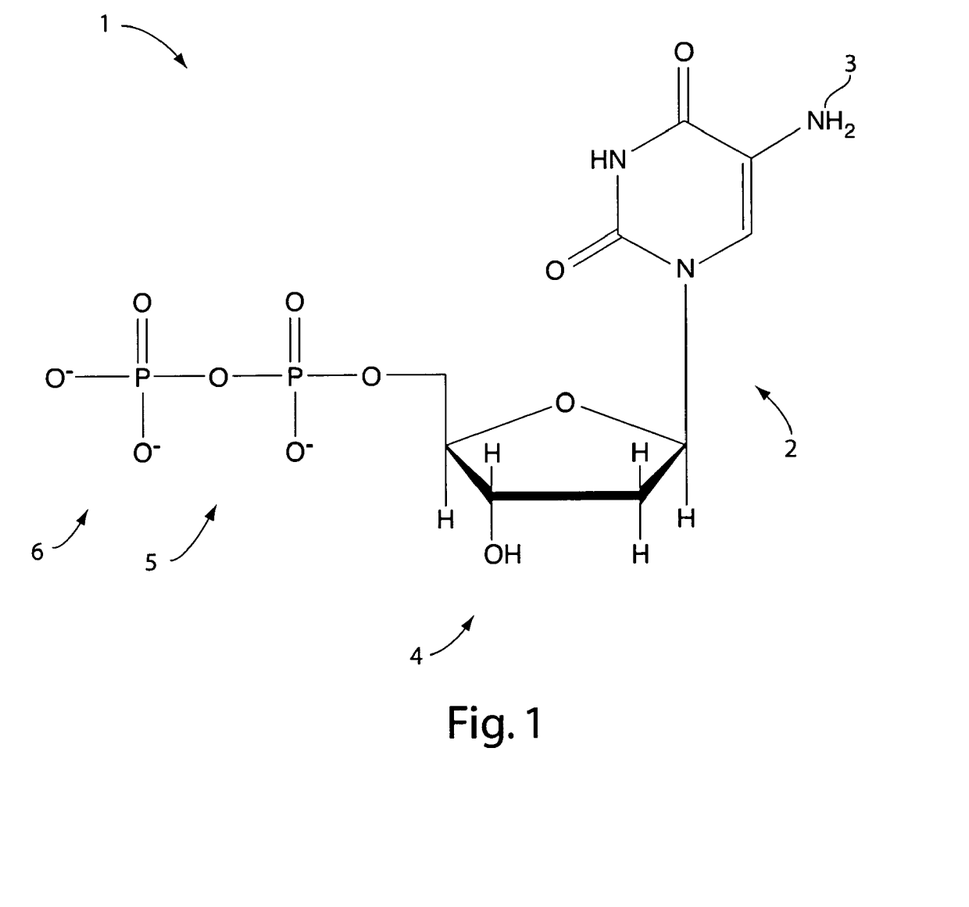
FIG. 1 is a structural diagram of one embodiment of the invention.

FIG. 1 illustrates 5-amino-2'-deoxyuridine diphosphate, in accordance with one embodiment of the invention. In this figure, modified uridine nucleotide 1 comprises a uridine moiety 2 having a 5-amino group 3, a 2'-deoxyribose sugar 4, and two phosphate groups 5, 6. As shown in FIG. 1, the nucleotide has two phosphate groups. However, in other embodiments of the invention, additional phosphate groups may also be present or the phosphate groups may be located in different positions. The phosphate groups may be located anywhere on the molecule, attached to each other or to different portions of the molecule, for example, on the 2'-carbon of the deoxyribose ring. In some embodiments, the phosphates may be attached to the 5'-end of the sugar, and arranged in a linear fashion.

The sugar of the nucleotide is shown in FIG. 1 as being deoxyribose. However, the sugar may be any sugar that can be incorporated into a nucleic acid. For example, other substituents may be present on the sugar, or the sugar may have a different number of atoms within the ring. For example, one or more fluorine atoms or hydroxide groups may be connected to the 2'- or 3'-carbon atoms of the sugar. Alternatively, the phosphate or the base may be connected to the sugar by an α linkage instead of a β linkage.

As shown in FIG. 1, the base is a uracil moiety having an attached amino group on the 5-carbon atom. However, the base may also be another pyrimidine, such as thymine. Any electron-rich group may be substituted onto the pyrimidine in any position, such as on the 5-carbon or 6-carbon atoms, for example, but not limited to, a hydroxide, a halogen such as fluorine or chlorine, an alkyl, an amino group, an alkylamino group, or a dialkylamino group. Adding an electron-rich substituent to the base may provide better stability in certain cases, for example, during elevated temperatures, such as may be encountered in a polymerase chain reaction device. The base may also have other substituents. For example, additional electron-rich substituents may be attached to the base to, for example, enhance stability of the molecule. As an example, a fluorine or a chlorine atom may be attached to the 6-carbon atom of a 5-aminouracil moiety. Alternatively, one or more of the oxygen atoms may be modified or replaced by another type of atom, for example, sulfur. Combinations of these substituents may also be envisioned.

It is to be understood that the modified nucleotides of the invention may have a wide range of variations. For example, other bases or sugars may be incorporated into the nucleotide. In other cases, other substituent groups may be added to the base or the sugar, for example, but not limited to, electron-rich, reactive or enzymatic moieties. Other moieties may include fluorescent moieties, such as fluorescein, or radioactive molecules, such as $^{14}$carbon or $^{35}$sulfur. Alternatively, a reporter molecule may be derivitized onto the nucleotide. For example, a protein, a small molecule such as biotin, or a catalyst such as green fluorescent protein ("GFP") may be attached to the nucleotide.

Figure 3:
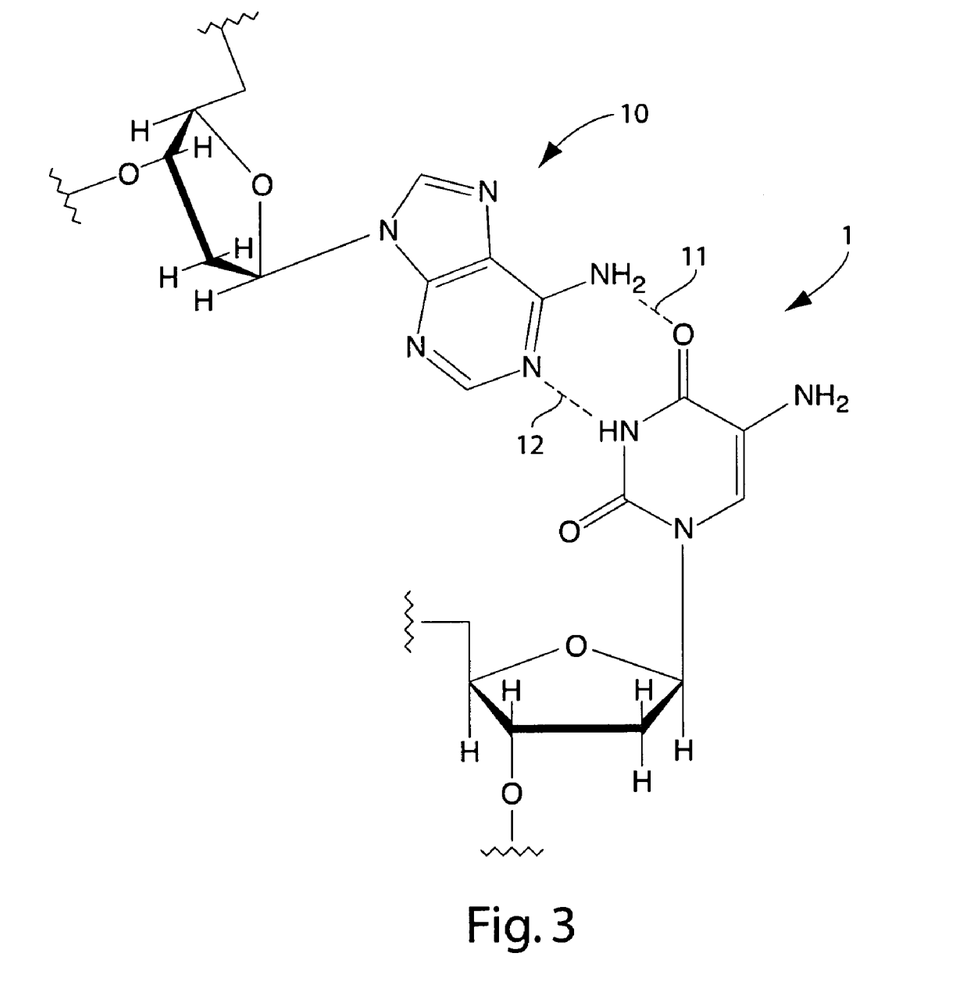
FIG. 3 is a structural diagram, showing how one embodiment of the invention may hydrogen-bind to an adenine base.
Figure 4:
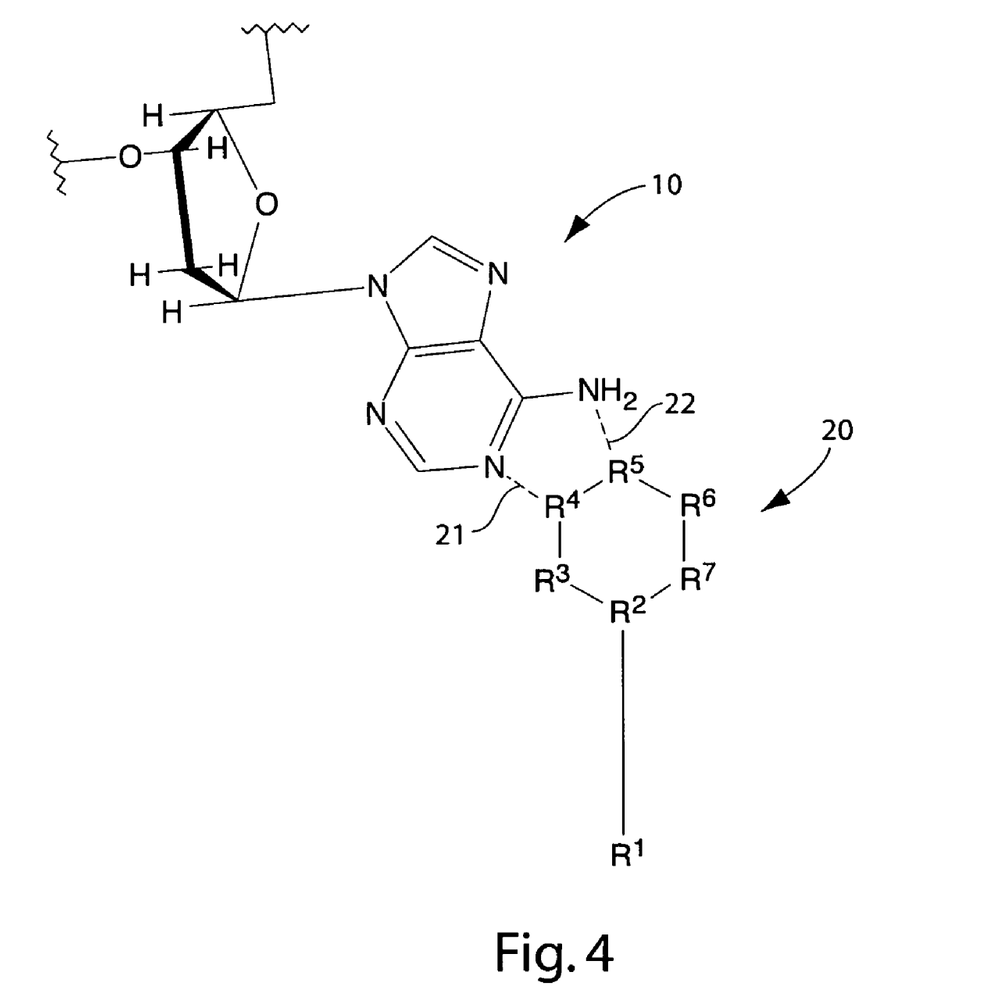
FIG. 4 is a structural diagram, showing how another embodiment of the invention may hydrogen-bind to an adenine base.

The above and other modifications may confer certain properties on the modified nucleotides of the invention. The modified nucleotides of the invention, in some cases, may be analogous to certain nucleic acid bases, such as uridine or thymine. In some cases, the analog has a structure, or an electronic configuration, similar to that of a natural nucleic acid base, and may not cause distortion of the nucleic acid strand or alteration of the secondary structure of the nucleic acid strand when introduced into the nucleic acid strand. In other cases, the modified nucleotides of the invention may participate in hydrogen-bonding to another nucleotide, such as hydrogen-bonding to an adenine base or an adenine analog. The 3-hydrogen and 4-oxygen atoms of the modified nucleotide may be able to hydrogen-bond to another nucleotide. For example, in FIG. 3, nucleotide 1 may hydrogen-bind to the 1-nitrogen atom or the 6-amino group of adenine base 10 through hydrogen bonds 11 and 12. FIG. 4 shows an adenine base 10 hydrogen bonding to groups $R^4$ and $R^5$ on molecule 20 through hydrogen bonds 21 and 22, respectively. Other hydrogen-bonding configurations may also be possible.

The modified nucleotides may also be targeted and cleaved as desired. In some cases, modified nucleotides which have been integrated into a nucleic acid strand may be cleaved without altering the rest of the nucleic acid strand. The modified nucleotides of the invention may be used, in some cases, to study the interaction between a nucleic acid and another molecule, or to study the structure of the nucleic acid. In other cases, the modified nucleotides of the invention may be used to sequence a nucleic acid. The modified nucleotides of the invention may also be used to expand the abilities of nucleic acids, for example, to introduce various chemical functionalities into a nucleic acid strand, without distorting its native confirmation.

The modified nucleotides of the invention may be synthesized and prepared using any suitable technique. For example, the modified nucleotides may be synthesized from deoxyuridine or a substituted deoxytiridine, such as 5-chloro-2'-deoxyuridine or 5-bromo-2'-deoxyuridine. The 5-amino group may be added to a substituted deoxyuridine to produce an aminated deoxyuridine using any suitable method, such as amination with an excess of ammonia under appropriate conditions. Alternatively, starting with a nitrated substituent, such as 5-nitro-2'-deoxyuridine, hydrogenation of the starting material over a palladium catalyst under hydrogen gas may also yield aminated deoxyuridines. Phosphorylation of aminated deoxyuridines may occur using any suitable technique, for example, reaction with a pyrophosphate, such as tributylamonium pyrophosphate. The number of deoxyuridine phosphorylation events may be controlled by any appropriate method, such as limiting the concentration of pyrophosphates or altering the reaction conditions.

It should be understood that the modified nucleotides of the present invention are not limited to only those nucleotides that can be produced using any of the above reactions. Alternative reaction pathways to produce 5-amino-2'-deoxyuridine or any of the other modified nucleotides of the present invention may also be contemplated. For instance, alternative phosphorylation or amination pathways may be envisioned, or the phosphorylation and amination steps may be reversed. Additional reaction pathways, for example, to add protecting or deprotecting groups or to add additional substituents, for example, to the uridine ring or to the amino group, may also be considered. Biologically-derived synthesis of the nucleotides may also be possible, for example, through the use of genetic engineering, such as through the use of various post-translational modification pathways.

The modified nucleotides may be added to a nucleic acid by any suitable technique. Examples of suitable techniques include polymerase chain reactions, solid-phase synthesis techniques, for example, with the use of a dimethoxytrityl protecting groups, or genetically engineering organisms, such as bacteria or mammalian cells. Dideoxy derivatives of the modified nucleotides may also be useful in certain forms of DNA synthesis. Polymerase chain reactions ("PCR"), for example, as described in Mullis et al., U.S. Pat. No. 4,965, 188 and incorporated herein by reference, may be particularly suitable for certain embodiments of the invention. One particular set of PCR conditions that may be useful include heating the reaction mixture including the nucleic acid to 94° C. for 3 minutes, then repeating the following procedure for a predetermined number of times, for example, 29 times: heating the mixture to 94° C. for 1 minute, cooling the mixture to 55° C. for 90 seconds, followed by warming the mixture to 72° C. for 90 seconds. A final annealing step of warming the mixture at 72° C. for 7 minutes may also be added. The modified nucleotides may be added to any position within the nucleic acid, and additional nucleotides (modified or unmodified) may further be added to the growing nucleic acid strand after modified nucleotides have been added. Other techniques for adding the modified nucleotide to a nucleic acid strand may be contemplated without departing from the scope of the invention, for example, using genetic engineering techniques, either in vitro or in vivo, such as within a genetically modified bacterium.

Figure 2:
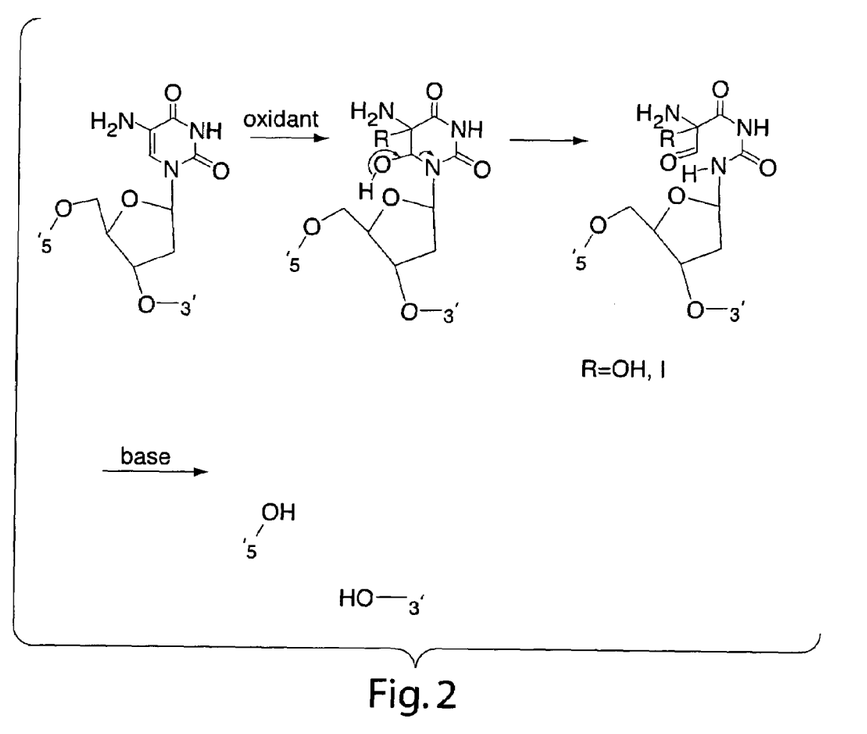
FIG. 2 is a reaction pathway of one embodiment of the invention.

Targeted cleavage of the modified nucleotides of the invention integrated in a nucleic acid may be useful in some cases, for example, to determine the structure or the composition of the nucleic acid. The modified nucleotides may be cleaved using any suitable technique, such as enzymatic cleavage using a restriction endonuclease. Some nucleotides may be particularly susceptible to cleavage by exposure to an oxidative agent and an alkaline compound. Exposure of the modified base to an oxidative agent followed by an alkaline compound may destroy or modify the base. An illustration of the reaction mechanism by which the modified nucleotide is cleaved is shown in FIG. 2. The oxidative agent may first attack the base near the electron-poor end of the pyrimidine ring, which may cause the pyrimidine ring to open. After the pyrimidine ring has been opened, exposure to an alkaline compound may cause the nucleotide to degrade. Any oxidative agent which may attack the modified nucleotide may be used, for example, potassium permanganate, hydrogen peroxide, potassium dichromate, aqueous periodates, or aqueous iodine. Similarly, any alkaline compound which may assist in cleavage of the modified base may be used; suitable alkaline compounds may include alkali metal hydroxides, such as sodium hydroxide or potassium hydroxide, or organic alkaline materials, such as piperidine, or pyrrolidine. There may be certain optimal concentrations of these alkaline compounds. For example, particularly useful concentrations of sodium hydroxide may be between 0.1 to 0.5 M preferably between 0.2 and 0.4 M. A suitable concentration of an organic alkaline may be between 5 and 15%, preferably between 8 and 12%. If the modified base is within a nucleic acid, the cleavage of the base by the oxidative agent and the alkaline compound may split the nucleic acid into two fragments, as shown in FIG. 2. In certain embodiments of the invention, this reaction may be used in sequencing the nucleic acid, or in determining how the nucleic acid interacts with proteins or other molecules, for example, as described below.

In one set of embodiments of the invention, the modified nucleotides may be used to measure or analyze interactions between nucleic acids and other molecules. The molecular interactions may be measured by any suitable technique, for example, DNA footprinting, as described in, for example, Larson et al., *Bioorganic Chemistry: Nucleic Acids*, Hecht, Ed., Oxford University Press, New York, 324–342 (1996). The other molecules may include proteins, such as proteins that bind noncovalently to DNA or RNA, smaller peptides, other nucleic acids, hormones, intercalating agents, or small molecules that may interact with nucleic acids. The small molecules typically have a molecular weight of less than about 2000 daltons, preferably less than about 1000 daltons. The modified nucleotides of the invention may be suitable for detecting and measuring various types of noncovalent interactions between the nucleic acid and other molecules, for example, but not limited to, ionic, van der Waals, entropic, steric, hydrogen-bond, or hydrophobic interactions and the like. For example, by substituting a modified nucleotide for a thymine or a uracil base on a nucleic acid, an interaction between the nucleic acid and another molecule may be altered in some fashion. Measurement of the change in the interaction may be useful in determining the degree of binding between the nucleic acid and the molecule, or the stereospecificity of the two molecules. Other molecular interactions may also be analyzed in this fashion, for example, but not limited to, DNAzyme/substrate, promoter/DNA, DNA/RNA, DNA/DNA, DNA/protein, DNA/transcription factor, DNA/enzyme, DNA/ribosome, DNA/ribozyme, and the like.

The modified nucleotides of the invention may also be used to determine the structure or the composition of a nucleic acid, such as DNA or RNA. Any technique may be used to determine the structure or the composition, for example, X-ray crystallography. The nucleotides of the invention may be used to sequence a nucleic acid. A sequence of nucleic acids incorporating the modified nucleotides of the invention may still continue to be grown by any suitable technique, as the modified nucleotides may not interfere or sterically hinder nucleic acids synthesis enzymes, such as polymerase. Thus, nucleic acid sequences may continue to be synthesized after incorporation of the modified nucleotides. As the modified nucleotides may not interfere with DNA synthesis, the distribution of the modified nucleotides within the growing nucleic acid strand can be controlled and may be distributed evenly within the nucleic acid strand.

The modified nucleotides incorporated into a nucleic acid may later be cleaved using a combination of a oxidative agent and any alkaline compound, as previously described. The resulting nucleic acid fragments may then be individually sequenced by any suitable technique. Comparison of the fragments may then be used to reconstruct the original nucleic acid sequence. As specific individual nucleotides may be targeted for cleavage using this technique, specific cleavage and sequencing of nucleic acids may be performed. The nucleic acids may be characterized by any suitable method of detecting or sequencing the nucleic acids. Suitable techniques may include, for example, but not limited to, capillary gel electrophoresis, radioactive labeling, fluorescent labeling, or other gel sequencing techniques.

In another set of embodiments of the invention, the modified nucleotides may be integrated within nucleic acids to expand the abilities of the nucleic acids to perform chemically. As a non-limiting example, nucleic acids having the modified bases of the invention may be used to produce novel ribozymes or DNAzymes. The novel ribozymes or DNAzymes may be designed, for example, by using directed evolution or by using computational design techniques, such as ab initio calculations. In other embodiments of the invention, the modified nucleotide may further be modified with, for example, additional functional groups, proteins, enzymes, fluorescent moieties, or radioactive atoms. The functional groups may be any functional group, such as an alkyl group. Additionally, two or more groups may be attached to the same base, providing additional functionalities. Further modifications may also be possible. By adding additional chemical groups to the modified nucleotide, additional properties or characteristics for the nucleotide or for the molecule incorporating the modified nucleotide may be provided in this fashion.

The function and advantages of these and other embodiments of the present invention will be more fully understood from the following examples. These examples are intended to be illustrative in nature and are not considered to be limiting the scope of the invention.

EXAMPLE 1

Synthesis of 5-amino-2'-deoxyuridine

This example demonstrates the synthesis of 5-amino-2'-deoxyuridine in one embodiment of the invention.

All reactions were run under argon unless otherwise indicated. 5-bromo-2'-deoxyuridine (3.0 g) was loaded into a steel bomb. The bomb was cooled to −78° C. and liquid ammonia (20 ml) was carefully added. The starting material dissolved readily. The bomb was then sealed and stirred at 55–60° C. After 44 hours, the bomb valve was released and ammonia allowed to boil off. Particular attention was paid to avoid vigorous boiling of ammonia to avoid loss of product. Precoated silica-gel plates were used to perform thin-layer chromatography ("TLC"). Detection was by exposure to ultraviolet light, or dipping the plates into 5% sulfuric acid in methanol, followed by heating to 200° C. TLC analysis using a 2:8 ratio of methanol to methylene chloride showed that the reaction was complete and only one product was formed.

Pyridine (25 ml) was added to the brown oil in the bomb and the resulting suspension was transferred to a 100 ml beaker. The bomb was washed with 3 ml pyridine, which were then added to the same beaker. Gravity filtration of this suspension afforded a white precipitate which was found to be ammonium bromide ($NH_4Br$).

The filtrate was concentrated in vacuo to an oil, which was diluted with methanol (10 ml) and added to silicon dioxide (20 ml). The resulting slurry was concentrated to dryness in vacuo and loaded onto a 3 cm diameter chromatographic column. The product was eluted with a methanol/methylene chloride solvent system (starting with 5% methanol in methylene chloride, and increasing linearly to 15% methanol). Appropriate fractions were pooled together and concentrated in vacuo. A white solid (1.54 g, 65% yield) was isolated and characterized.

Nuclear magnetic resonance ("NMR") was recorded at 500 MHz for $^1$H-NMR recorded and 400 MHz for $^{13}$C-NMR. NMR analysis of the white solid is as follows: $R_f$(MeOH:DCM=2:8) 0.26, UV: $\lambda_{max}$=294 nm, $\epsilon$=7400. $^1$H-NMR ($CD_3OD$): 7.22 ppm (s, 1H), 6.28 ppm (t, 1H), 4.33 ppm (dd, 1H), 3.83 ppm (ddd, 1H), 3.69 ppm (dd, 2H), 2.15 ppm (ddd, 2H). $^1$H-NMR($^6$d-DMSO): 11.35 ppm (s, 1H), 6.92 ppm (s, 1H), 6.19 ppm (s, 1H), 5.21 ppm (s, 1H), 4.91 ppm (s, 1H), 4.18 ppm (dd, 1H), 4.14 ppm (s, 1H), 3.72 ppm (ddd, 1H), 3.42 ppm (dd, 2H), 3.18 ppm (s, 1H), 1.95 ppm (ddd, 2H).

Thus, this example demonstrates the synthesis of 5-amino-2'-deoxyuridine, according to one embodiment of the invention.

EXAMPLE 2

Synthesis of
5-amino-2'-deoxyuridine-5'-triphosphate

This example illustrates the synthesis of 5-amino-2'-deoxyuridine-5'-triphosphate from 5-amino-2'-deoxyuridine, according to an embodiment of the invention.

5-amino-2'-deoxyuridine and anhydrous tributylammonium pyrophosphate were thoroughly dried before use by storing them in a desiccator charged with $P_4O_{10}$ under high vacuum for 3 days. Tributylammonium pyrophosphate and $PO(CH_3O)_3$ were dried on $CaH_2$ overnight and then distilled at reduced pressure (house vacuum).

5-amino-2'-deoxyuridine (330 mg) was dissolved in $PO(CH_3O)_3$ (2.7 mL) in a flame dried 25 ml flask. The resulting pale-yellow solution was cooled to −15° C. and $POCl_3$ (190 μl) was slowly added. The contents of the flask were stirred at −10° C. for 3 hours with periodical monitoring of reaction progress by TLC, using procedures similar to those described above.

After 3 hours, the flask was subject to high vacuum for 15 minutes, keeping the flask at 0° C., to remove unreacted $POCl_3$. A solution of tributylammonium pyrophosphate (1.24 g) in dry dimethylformamide (13.58 mL) was added to the reaction mixture, and the mixture was stirred for 2 minutes at 0° C. The mixture was then quenched with 1.5 M tetraethylammonium bromide (20 ml, pH=7.5), and further stirred at room temperature for 30 minutes.

The reaction mixture was lyophilized three times, then purified by ion-exchange chromatography using linear gradient of 1.5 M tetraethylammonium bromide. The ion exchange chromatography settings included a flow rate of 5 ml/min over diethylaminoethyl ("DEAE") SEPHADEX™ A-25 beads (Pharmacia Corp., Peapack, N.J.), with detection at 254 nm.

Part of the isolated triphosphate was then lyophilized 5 times and further purified by HPLC. HPLC conditions included a flowrate of 2 ml/min over ODS ULTRASPHERE™ (10×250 mm, Beckman Coulter, Inc., Fullerton, Calif.), with detection at 294 nm. The solvent system included 100 mM triethylamine acetate ("TEAA") and $CH_3CN$ in the following proportions: 1.5% $CH_3CN$ (0 to 10 min), linear gradient to 4% $CH_3CN$ (10 to 40 min), linear gradient to 10% $CH_3CN$ (40 to 41 min), 10% $CH_3CN$ (41 to 55 min), linear gradient to 1.5% $CH_3CN$ (55 to 56 min) and 1.5% $CH_3CN$ (56 to 65 min). Isolated yielded 25 mg of HPLC-purified, hygroscopic white crystals.

Analytical HPLC conditions included a flowrate of 1 ml/min with detection at 294 nm over an ODS ULTRASPHERE™ 5 μm $C_{18}$ column (4.6×250 mm). The solvent system used 100 mM TEAA (pH=7.0) with a linear gradient (0 to 15% $CH_3CN$) over 25 min. Analysis of the product was as follows: $R_f$(isopropanol:water:ammonia=6:2:2) 0.16, with an analytical HPLC retention time of 9.7 minutes. $^1$H-NMR ($NH_4HCO_3$/($NH_4$)$_2CO_3$ buffer, pH=8.5 in $D_2O$): 7.46 ppm (s, 1H), 6.36 ppm (t, 1H), 4.21 ppm (dd, 1H), 4.17 ppm (dd, 2H), 2.37 ppm (ddd, 2H). $^{31}$P-NMR ($NH_4HCO_3$/($NH_4$)$_2CO_3$ buffer, pH=8.5 in $D_2O$): −9.7 ppm (d), −10.45 ppm (d), −22.3 ppm (t).

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention. In the claims, all transitional phrases or phrases of inclusion, such as "comprising," "including," "carrying," "having," "containing," and the like are to be understood to be open-ended, i.e. to mean "including but not limited to." Only the transitional phrases or phrases of inclusion "consisting of" and "consisting essentially of" are to be interpreted as closed or semi-closed phrases, respectively.

What is claimed is:

1. A method of synthesizing a compound, comprising:
providing a species comprising a nucleoside; and
reacting the species with a first compound to form a second compound comprising a structure:

wherein n is at least 2.

2. The method of synthesizing a compound of claim 1, wherein the nucleoside comprises deoxyuridine.

3. The method of synthesizing a compound of claim 1, wherein the nucleoside comprises 5-nitro-2'-deoxyuridine.

4. A method of synthesizing a nucleotide, comprising:
providing a first compound comprising a structure:

wherein n is at least 2; and
reacting the $NH_2$ group of the first compound with a second compound to form a nucleotide comprising a structure:

$R^1$ and $R^2$ each comprising an atom, wherein at least one of $R^1$ and $R^2$ comprises a carbon atom.

5. The method of synthesizing a nucleotide of claim 4, wherein at least one of $R^1$ and $R^2$ comprises a fluorescent entity.

6. The method of synthesizing a nucleotide of claim 4, wherein at least one of $R^1$ and $R^2$ comprises a radioactive entity.

* * * * *